United States Patent [19]

Willoughby et al.

[11] Patent Number: 4,977,785

[45] Date of Patent: Dec. 18, 1990

[54] METHOD AND APPARATUS FOR INTRODUCTION OF FLUID STREAMS INTO MASS SPECTROMETERS AND OTHER GAS PHASE DETECTORS

[75] Inventors: Ross C. Willoughby; James D. Buchner, both of Pittsburgh, Pa.

[73] Assignee: Extrel Corporation, Pittsburgh, Pa.

[21] Appl. No.: 157,626

[22] Filed: Feb. 19, 1988

[51] Int. Cl.⁵ .............................................. G01N 1/34
[52] U.S. Cl. ............................... 73/863.12; 250/288; 250/429; 55/17; 239/86; 261/78.2
[58] Field of Search ................. 250/288, 288 A, 283, 250/429, 430; 73/865, 863.12, 864.81, 864.85; 239/86; 55/17, 270; 261/78.2

[56] References Cited

U.S. PATENT DOCUMENTS

| | | | |
|---|---|---|---|
| 3,944,826 | 3/1976 | Gray | 250/288 |
| 3,997,298 | 12/1976 | McLafferty et al. | 250/288 A X |
| 4,160,161 | 7/1979 | Horton | 250/283 X |
| 4,298,795 | 11/1981 | Takeuchi et al. | 250/282 |
| 4,358,302 | 11/1982 | Dahneke | 250/288 X |
| 4,383,171 | 5/1983 | Sinha et al. | 250/288 X |
| 4,531,056 | 7/1985 | Labowsky et al. | 250/288 A |
| 4,607,163 | 8/1986 | Mizuno | 250/288 A |
| 4,629,478 | 12/1986 | Browner et al. | 250/288 A X |
| 4,687,929 | 8/1987 | Browner et al. | 250/282 |
| 4,762,995 | 8/1988 | Browner et al. | 250/288 A X |
| 4,861,988 | 8/1989 | Henion et al. | 250/288 A |
| 4,891,515 | 1/1990 | Jones et al. | 250/288 A |
| 4,916,077 | 4/1990 | Forster et al. | 261/78.2 X |

*Primary Examiner*—Tom Noland
*Attorney, Agent, or Firm*—Penrose Lucas Albright

[57] ABSTRACT

Methods and apparatus for introduction of sample from a flowing stream into mass spectrometers or other analyzing apparatus for analytical and process stream analysis of the sample. The apparatus generates an aerosol during the decompression of a gas, liquid or supercritical fluid stream. The aerosol's properties are dependent upon mass flow, pressure, temperature, solubility of sample, and the physical dimensions of the aerosol generating device. Upon aerosol generation, a less volatile sample in the form of condensed particles is separated from the gaseous components by accelerating the aerosol through a nozzle restrictor and utilizing momentum differences between solute particles and carrier gas molecules to obtain high solute enrichments at various particles or gas-phase detectors. The device functions primarily as an interface between a supercritical fluid chromatograph and the mass spectrometer.

12 Claims, 6 Drawing Sheets

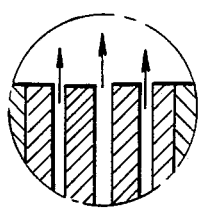
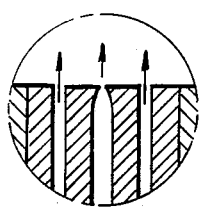
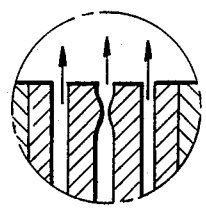
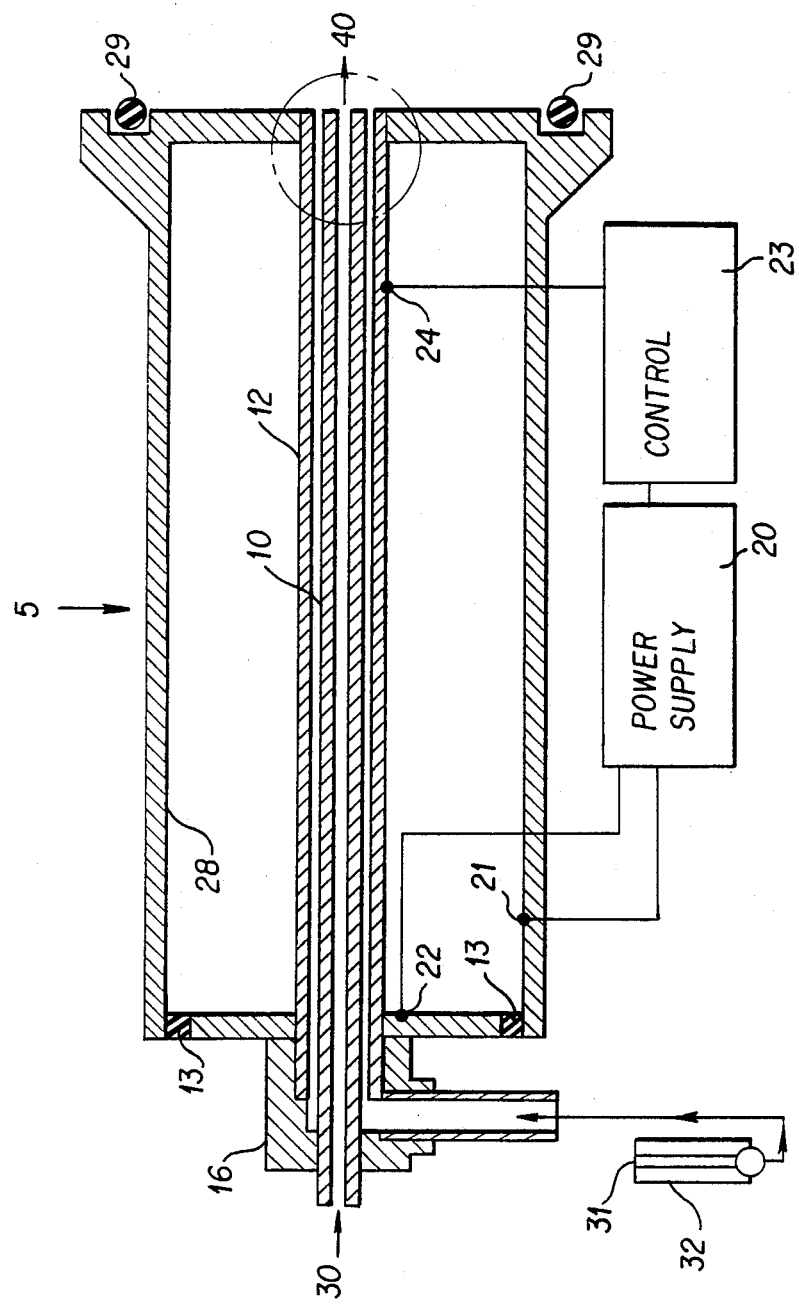

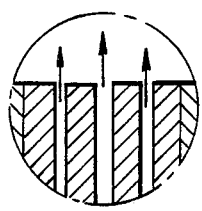
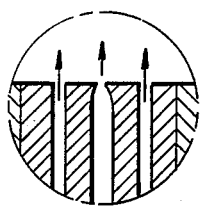
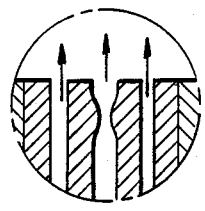
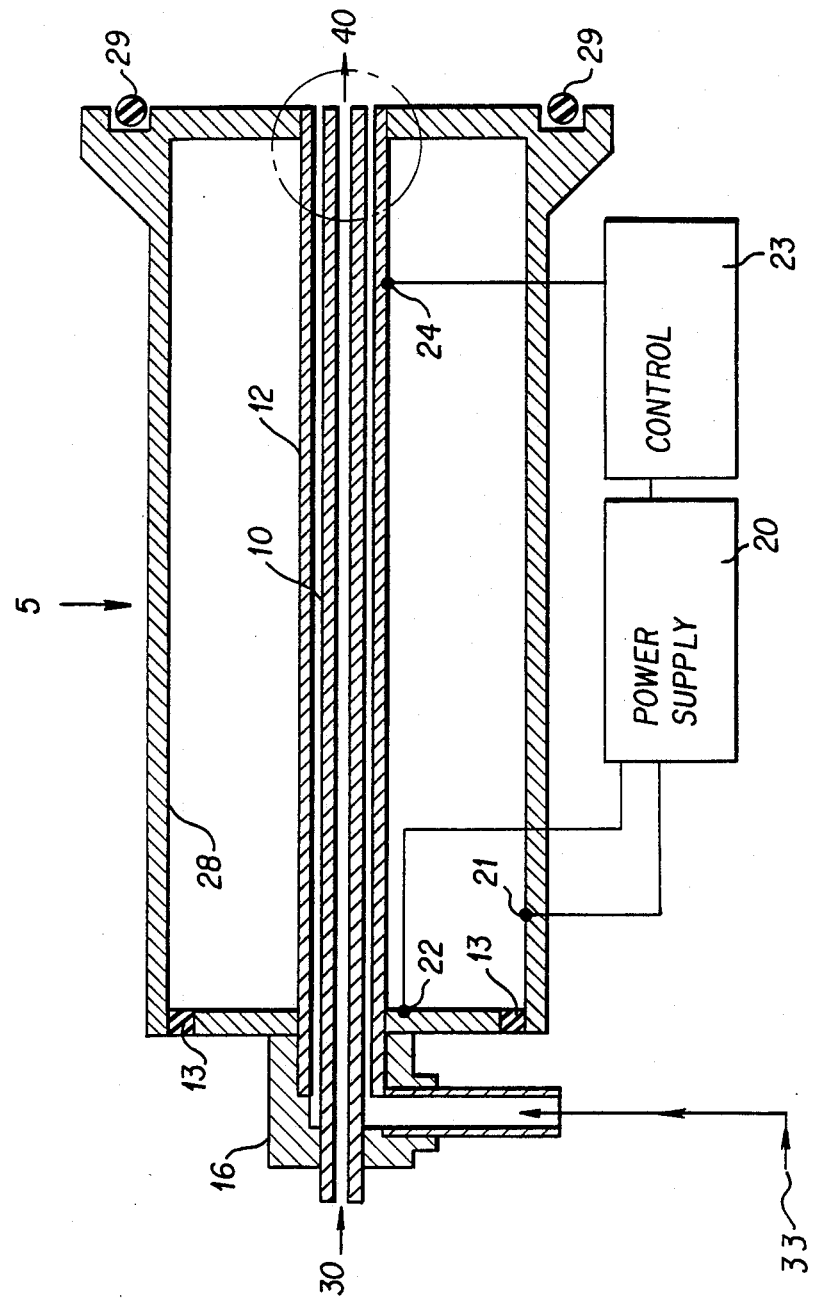

METHOD AND APPARATUS FOR INTRODUCTION OF FLUID STREAMS INTO MASS SPECTROMETERS AND OTHER GAS PHASE DETECTORS

FIELD OF THE INVENTION

The invention relates to apparatus and associated methods for introducing aerosol samples into mass spectrometers and/or other analytical instruments for analyzing the components of the samples and particularly to apparatus, which utilize one or several concentric capillary tubes which carry and control supercritical fluid.

Flow streams can be derived from gases, liquids, or supercritical fluids. The introduction of sample from flowing streams into gas phase or particle detectors is highly dependent upon the interface between the flow stream and the detector. This invention is primarily, but not limited to, the interface between a stream under supercritical fluid conditions or a liquid stream and a mass spectrometer (MS).

A supercritical fluid is a fluid in a highly compressed state having densities, diffusion coefficients, and viscosities intermediate between the gas and liquid states. At the critical temperature of a substance, the vapor and liquid phases have identical densities and the gas cannot be liquified irrespective of the pressure applied. Above the critical temperature and pressure, the substance exists as a supercritical fluid (1,2). Supercritical fluids have solvating properties approaching that of a liquid.

Any flowing stream can be the mobile phase of a chromatographic system if the mobile phase is permitted to pass through a stationary phase which itself has particular affinity characteristics towards specific sample components. Using chromatographic separation techniques (3), it is possible spatially and temporally to resolve components in a multi-component mixture due to differences in partition coefficients.

Gas Chromatography (GC) separates components as a function of partitioning between a stationary phase and a gas phase and therefore has limitations with respect to solute volatility. Analytes must have appreciable vapor pressure to be analyzed using this technique. Liquid Chromatography (LC) utilizes a liquid as a mobile phase. Inasmuch as the nature of this liquid is an experimental parameter, virtually any soluble compound can be analyzed using this technique. However, because the diffusion coefficients of liquids are low compared to gases, and the densities are high compared to gases, it is difficult to use capillary columns (long narrow open tubes with stationary phase on the inner walls) in LC which are the most efficient at resolving multi-component mixtures in GC (4) But in view of the circumstance that supercritical fluids have physical properties intermediate to gases and liquids, capillary column techniques are compatible with supercritical fluids. Therefore Supercritical Fluid Chromatography (SFC) has advantages over GC in the ability to separate nonvolatile or thermally labile compounds and advantages over LC in terms of resolving capabilities (5,6).

The operation of an SFC/MS interface requires that the mobile phase undergo a pressure reduction stage and ionization of the analyte prior to mass analysis. To be able to ionize analyte in a unimolecular fashion (under electron impact conditions), pressure in the mass spectrometer must be kept in the 10E-5 torr range. Even narrow bore capillary columns used in SFC can produce flow rates over 20 atmospheric milliliters per minute (mL/min)(7). Packed columns produce substantially higher volumetric flow rates in the range of up to several hundred atmospheric mL/min. Because packed columns can accept more sample and, when well constructed operate with more resolving power per unit time than their capillary analogs (8), higher flow rate SFC/MS interfacing should be considered important Therefore, due to basic flow rate incompatibility between various SFC techniques and MS, a sample enrichment stage within the interface appears desirable.

The process of expanding a supercritical fluid to lower pressures necessary for sample introduction into mass spectrometers has been described in detail (9). Depending upon the nature of the restrictor (length, diameter, geometry) which creates sufficient back-pressure in order to maintain supercritical conditions upstream of the mass spectrometer, and the temperature of this restrictor device, particles of various size distribution are formed in this decompression region. Generally these particles are carbon dioxide clusters generated in the decompression region and have been considered undesirable. Various techniques have been employed to decluster or evaporate these particles such as rigorous heating of a restrictor nozzle. Particles of larger diameter may increase detector noise. Clusters of analyte with carbon dioxide have presented problems in obtaining unimolecular 70 electron volt ionization with good sensitivity using Direct Fluid Introduction (DFI) (10, 11). In DFI SFC/MS, the fluid is allowed to expand directly into the ion source of the mass spectrometer through a micron sized restrictor. Therefore, most DFI SFC/MS is performed under chemical ionization conditions where the pressure is 0.5-3 torr and clusters are broken down via collisions with gas molecules prior to and during ionization (12-15). Micron sized restrictors can be easily plugged and produce erratic analyte delivery, especially when attempting analysis of nonvolatile high molecular weight materials that have been reported to coat restrictor surfaces. Eliminating the requirement for micron sized restrictors should therefore, provide significant advantages.

In one embodiment of the present invention the supercritical fluid is permitted to expand into a liquid medium. Liquids being less compressible than supercritical fluids, sufficient back-pressure can be produced by pumping the liquid through a less restrictive capillary tube to maintain supercritical conditions within that flow stream and therefore retain the supercritical solvency until analytes can be dissolved within the liquid stream. Solute dissolved in a suitable liquid stream, are then desolated by a number of techniques; including, but not limited to thermal nebulization and aerosol generation (19). Aerosol generation is assisted by the pneumatic nebulization produced by the expanding supercritical or gas stream often leading to smaller particle sizes and the associated benefits. Therefore, the present invention results in improving nebulizer performance where the liquid stream is the analytically significant stream.

Once particles have been formed either by evaporation of liquid droplets as described above or by fluid decompression, the present invention generates a well directed high velocity particle beam to carry analyte preferentially compared to the gaseous component of the aerosol stream, into the mass spectrometer ion source or other gas phase detector. This is accomplished by allowing the aerosol stream, a heterogeneous mixture of particles and gas, to flow through a physical restriction and expand into a lower pressure region forming an aerosol beam. Because the particles have a much higher mass and also momentum than the expanding gases an enriched solute sample is obtained by skimming the core of this aerosol beam. The skimmed core of the beam is termed "particle beam" and is directed toward appropriate detectors.

An aerosol generated from a gas or supercritical fluid stream which utilizes particle beam solute enrichment to introduce sample into various detectors appears novel, as such. However, Randall and Wahrafting (16) constructed a molecular beam enrichment interface for SFC/MS. Whereas, it is not inconceivable that particles or clusters could have been detected using this system, the beam was presented coaxially to the mass filter so that gas phase neutral species could be sampled and ionized. Further, the supercritical fluid was expanded into a relatively low pressure region, whereby the majority of sample was removed by pumping in the expansion region. Consequently, inefficient solute transport into the ion source of the mass spectrometer resulted. In this regard, the interface functioned more like a sample splitter. With pressures in the region of interest being 0.01 torr or less, the majority of particles formed are lost due to impaction on the expansion chamber walls.

Smith and Udseth (17) have recently described an interface which is capable of higher volumetric flow rate SFC interfacing. Here again this interface is oriented axially with respect to the mass filter so particles generated and transmitted into the source region cannot be easily evaporated for lower pressure unimolecular EI ionization. The supercritical fluid is expanded into a lower pressure (10-50 torr) region with multiple pumping pathways which limits sample transmission through the interface into the ion source due to stream splitting in a similar fashion to the work of Randall and Wahrhaftig (16).

In view of the foregoing, to improve sample detection, it was considered that a need existed for an aerosol generation technique for SFC whereby the micron sized restrictor could be substantially eliminated, thus minimizing potential clogging of micron sized restrictors currently used in SFC. At the same time, it was considered desirable to take advantage of momentum differences between particle and gas phases in an expanding aerosol beam to produce a highly enriched solute particle beam for introduction into various gas phase or particle detectors. Enrichment of analyte from the solvent with high analyte mass transport enables low nanogram (ppm–ppb) analysis using electron impact ionization techniques which has been heretofore difficult to obtain due to cluster formation. In addition, higher volumetric flow rates experienced with larger diameter packed SFC columns would be accommodated. Embodiments of this interface capable of handling flow rates of up to ten atmospheric liters per minute would be advantageous.

Several interfaces utilizing particle beam solute enrichment have been described for LC/MS (18, 19). However, neither of the prior art patents consider application to SFC/MS nor the other novel nebulizer embodiments which are objectives of the present invention.

Other interfacing techniques for SFC/MS have been described in the general literature and are included here for completeness. Games, et al have described an interface (20) used in LC/MS. Particles are undoubtedly formed in this technique but no attempt is made at enrichment of solute prior to ionization.

Henion, et al have used an atmospheric pressure ionization source for SFC/MS (21). Although good sensitivities have been demonstrated using this technique, it is limited to chemical ionization processes which alone are insufficient for structural elucidation.

The following information is presented as a bibliography and is incorporated by reference herein.

(1) C.M. White, R. K. Houck, J.HRC & CC, 9, 3016.
(2) H. H. Lauer, D. McManigill, R.D. Board, Anal. Chem., 55, 1370–1375 (1983).
(3) R. L. Grob, Modern Practice of Gas Chromatography; Wiley, New York, (1977).
(4) L S Ettre, Introduction to Open Tubular Columns, Perkin Elmer Corp, Norwalk, CT (1978).
(5) J. C. Fieldsted, M.L. Lee, Anal. Chem, 56. 619–628A (1984).
(6) M. Novotny, M.L. Lee, U.S. Pat. No. 4,479,380; filed Oct. 30, 1984; issued Mar. 9, 1987.
(7) B. W. Wright, et al, J. HRC & CC, 9, 145–153 (1986).
(8) H. E. Schwartz, LC/GC, 5, 490–497 (1987).
(9) R. D. Smith, et al, Anal. Chem, 58. 2057–2064 (1986).
(10) G. Holzer, S. Deluca, and K.J. Voorhees, J. HRC & CC, Vol. 8, p. 528, September 1985.
(11) R. D. Smith, et al, Anal. Chem., 56, 2973–2974 (1984).
(12) R. D. Smith, et al, Anal. Chem., 56, 2476–2480 (1984).
(13) R. D. Smith, H. R. Udseth, Anal. Chem., 55, 2266–2272 (1983).
(14) R. D. Smith, J.C. Fjeldsted, M.L. Lee, J. Chromatogr., 247, 231–243 (1982).
(15) E.D. Smith, J.D. Henion, J. HRC & CC, 9, 172–174 (1986).
(16) L.G.Randall, A. L. Wahrhaftig, Rev. Sci. Instrum., 52 (9), 1283–1295 (1981).
(17) R. D. Smith, H. R. Udseth, Anal. Chem., 59, 13–22 (1987).
(18) R. C. Willoughby, R.F. Browner; U.S. Pat. No. 4,629,478, of Dec. 16, 1986, and continuations.
(19) R. C. Willoughby, U.S. Pat. No. application Ser. No. 022,725, filed Mar. 6, 1987, and now abandoned and continued as a file wrapper continuation in Ser. No. 393,846, filed Aug. 14, 1989.
(20) D. E. Games, et al, Eur. Chrom. News, 1, 1 (1987).
(21) J. D. Henion, L. Wiedolf, E.D. Lee, T.R. Covey 35th ASMS Conf. on Mass Spec and Allied Topics Denver Col., May 24–29, 1987.

SUMMARY OF THE INVENTION

The invention involves a method and apparatus for introducing into analytical devices effluent from supercritical fluid, liquid, and gas streams, such as chromatographic streams, into gas-phase or particle detectors. It is applicable to sample introduction into a variety of analytical devices including mass spectrometers, flame ionization detectors, light scattering detectors, and other apparatuses suitable for determining the nature of analytes in the gaseous or particulate states.

Basic processes occurring in the present device are aerosol generation, solute enrichment, and detection of solute by a suitable gas-phase or particle detector.

One mechanism of aerosol generation with the present invention is obtained by flow of supercritical fluid or gas into a low pressure decompression chamber creating ideal conditions for condensation and cluster particle formation. The effluent is heated or cooled at or near the expansion region to control more precisely the thermodynamic process of aerosol generation. In one embodiment of this device, concentric flow of a conductive gas around the flow of supercritical fluid or gas better controls the flow of heat to and from the decompression region of the aerosol generator. A second embodiment utilizes liquid nebulization in the decompression region. The liquid flow serves as a source of backpressure exerted upon the supercritical flow stream which maintains the phase density and therefore the analyte solubility in the stream. Aerosol generation processes with this device involving liquid flow are enhanced in two ways. In the case where a supercritical fluid carries the analyte, the liquid stream may serve to provide surface for condensation of the analyte. In the case where the liquid stream carries the analyte, the supercritical fluid or gas streams may provide significant energy in nebulizing the liquid and generation of small diameter liquid droplets.

Solute enrichment occurs due to momentum differences between the gaseous and particulate components of the aerosol. Upon acceleration of the aerosol through a nozzle restriction into a vacuum region, radial expansion of the gaseous components of the aerosol occurs far more rapidly than the radial expansion of solute particles. This difference in radial expansion permits skimming a highly enriched solute particle beam on the axis of the aerosol beam. An alternative solute enrichment device uses cryotrapping of gaseous components of the aerosol while passing particulates onward to subsequent detection. Detection of the enriched solutes with the present device is accomplished by a variety of means. One embodiment of the invention uses particle beam enrichment to direct solute particles into the ion source of the mass spectrometer. The solute particle beam is intersected by sources which may include primary ion beams, discharge plasmas, electron beams, electric fields, or magnetic fields. Under these operating conditions, energy for solute evaporation and ionization is provided directly to solute particles during flight. Another embodiment utilizes a target surface to collect the solute particles. The target surface is generally composed of an inert material at a controlled temperature and serves to conduct heat to the particles for obtaining rapid solute vaporization. Once the solute is vaporized, normal gas phase processes provide ionization such as electron impact or chemical ionization. Alternatively, target materials may be chosen and run at sufficiently high temperatures where the work functions to ionize the molecule at the surface of the target is an energetically favored process. A target surface with collected particles may also be bombarded with ions, neutral, or electron beams to create gas-phase ions from the target surface. Alternatively, the solute is collected on a cold target surface for a period of time before heating the target, thus concentrating the sample to lower the detection limits. Measurement of power supplied to the target can also be used to determine the thermal properties of sample components such as heat of vaporization.

The use of other gas-phase detectors such as the flame ionization detector (FID) require pumping for solute enrichment and hydrogen as an aerosol generation gas. This embodiment operates with atmospheric or low pressure flames.

The particle beam embodiment is also used with laser scattered or continuum light scattering measurements and functions as a universal detector.

The invention is illustrated in preferred embodiments in the accompanying drawings.

BRIEF DESCRIPTION OF DRAWINGS

FIG. 2 is a view similar to FIG. 1 of a dual capillary decompression aerosol generator with conductive ga flow concentric to the sample stream;

FIGS. 2A, 2B and 2C are enlarged views of alternative tip geometries for the FIG. 2 generator;

FIG. 3 is a view, similar to FIGS. 1 and 2, of a dual capillary decompression aerosol generator with sheath liquid flow concentric to the sample stream;

FIGS. 3A, 3B and 3C are enlarged views of alternative tip geometries for the FIG. 3 generator;

DETAILED DESCRIPTION OF THE PREFERRED EMBODIMENTS

The following description sets forth the best modes for carrying out the inventive concepts disclosed The present invention pertains to methods and various types of apparatus for sample introduction of effluent from a supercritical fluid or gas stream into a mass spectrometer or other gas phase or particle detectors. The methods utilize the combination of decompression aerosol generation and momentum separation to transport highly enriched solute particles into various detectors. Three process are disclosed: (1) aerosol generation, (2) viscous aerosol transport and (3) aerosol beam momentum separation. The apparatus is thus presented in three components: (1) an aerosol generator, (2) a solute enricher, and (3) a solute collector or detector.

Referring to FIGS. 1 through 4, the portion of the invention that generates solvent depleted solute particles, referred to in the art as an aerosol generator and designated generally by reference number 5, comprises a capillary restrictor, which may be made of cylindrical fused silica, glass, metal tubing or any other appropriate material with the restrictor tip being either capillary, converging or supersonic in geometry In the various embodiments of this device, the capillary restrictor may be sheathed by one or more other capillary tubes in order coaxially to transport nebulization gases, heat conduction gases, or liquid; the exact configuration of which is determined by the specific application of the aerosol generator. The tubular flow of various fluids through the coaxial tubes are interchangeable (e.g. the inner capillary may confine the supercritical fluid, gas or liquid flow).

Figure 1A:
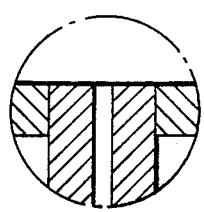
FIGS. 1A, 1B and 1C are enlarged views of tip configurations for the FIG. 1 generator.
Figure 1B:
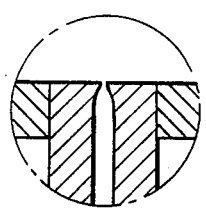
Figure 1C:
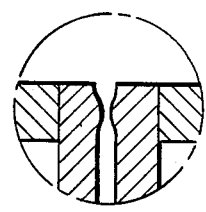
Figure 1:
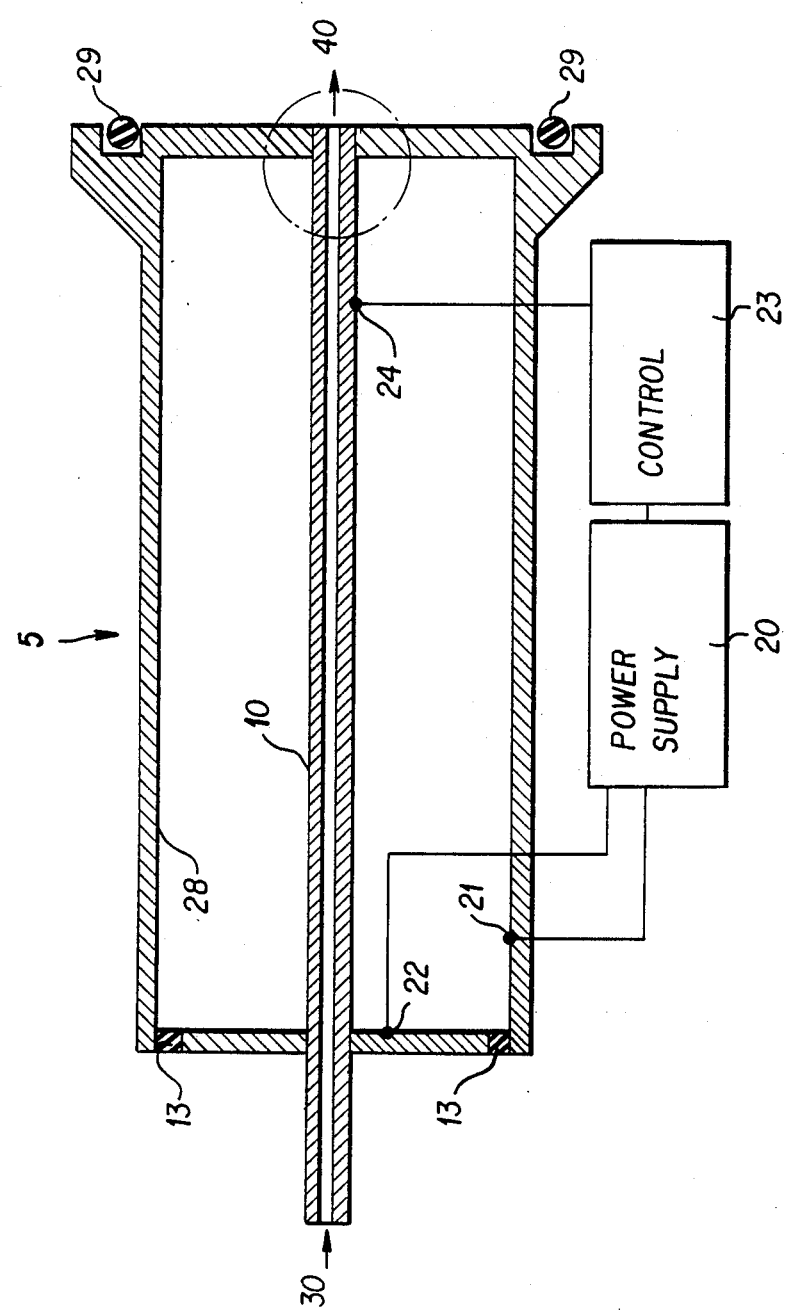
FIG. 1 is a diagrammatical sectional view of a single capillary decompression aerosol generator.

FIG. 1 illustrates a typical embodiment of the invention wherein the aerosol generator 5 has a single tube cylindrical capillary configuration comprising a single tube metal capillary restrictor 10 through which supercritical fluid or gas flows from supply 30 into the decompression chamber 40. A typical restrictor 10, as shown, is a twenty-five micrometer i.d. stainless steel tube. The tip of the capillary restrictor 10 is either a capillary nozzle as shown in FIG. 1A, a converging nozzle as shown in FIG. 1B, or a supersonic nozzle as shown in FIG. 1C. Aerosol is generated by rapid decompression of high density solute laden supercritical fluid or gases into the decompression chamber 40. Thermodynamic processes at the tip of the aerosol generator are controlled by either adding or removing heat from the flowing supercritical fluid or gas stream. In the embodiment shown in FIG. 1, the metal capillary restrictor 10 is heated resistively by means of power supply 20. Electrical connections are made at points 21 and 22. For capillary restrictor 10 to be part of the resistive heating circuit, electrical connections 21 and 22 are isolated by a ring insulator 13. The temperature of the aerosol generator is controlled by a feedback sensor 24 to a heater controller 23, feedback sensor 24 being a thermocouple. Other appropriate temperature feedback and control apparatus may also be used as will occur to one skilled in the art. Aerosol generator 5 is encased for safety by outer casing 28 and attached to the decompression chamber 40 at seal 29, said seal being a vacuum seal such as an 0-ring seal or other appropriate vacuum connection.

FIG. 2 illustrates a typical embodiment of the invention wherein aerosol generator 5 comprises a dual-tube cylindrical capillary configuration; comprising an inner capillary 10 through which the supercritical fluid or gas flows from supply 30 into the decompression chamber 40, and an outer capillary 12 confining the interstitial flow of sheath gas from supply 31 into decompression chamber 40. The function of the sheath gas is to conduct heat across the interstitial space between the inner and outer capillary tubes 10 and 12. Consequently, it functions as a means for heating or cooling supercritical fluid or gas flow stream which transmits through inner capillary 10. The sheath gas is preferred to be, but not limited to, a high thermal conductive material such as helium or hydrogen. In addition, the sheath gas serves to form a shield that surrounds the aerosol as it expands into decompression chamber 40. Flow of the sheath gas is controlled by sheath gas flow control 32. Flow tubes from supercritical fluid or gas supply 30 and sheath gas supply 31 intersect in a tee union 16 where the flow emerges therefrom in an orientation which is a function of the relative positioning of the capillary restrictors 10 and 12. Capillary restrictor 10 may have a restrictor tip that is of capillary geometry as shown in FIG. 2A, converging geometry as shown in FIG. 2B, or supersonic geometry as shown in FIG. 2C. Capillary tube 12 may also have restrictor tips of the configurations shown in FIGS. 2A, 2B and 2C. This particular embodiment of the aerosol generator section of the present device utilizes resistive heating of outer capillary 12, such outer capillary being, but not limited to, a conductive material such as nickel or stainless steel. The location of the end of the tube 10 relative to the end of tube 12 may be varied by adjusting their relative lateral dispositions by minor amounts, within limits, to produce different dispersion of the emerging aerosol in a manner comparable to well-known hose nozzles. Power supply 20 supplies sufficient wattage to heat outer capillary 12, the highest resistance component in the electrical circuit, with electrical connections at points 21 and 22 and electrical isolation by ring insulator 13, as before.

Again, the aerosol generator is encased for safety by outer casing 28 and attached to the decompression chamber 40 at seal 29, said seal being a vacuum seal such as an 0-ring seal or other appropriate vacuum connection.

FIG. 3 illustrates a typical embodiment of the invention wherein aerosol generator 5 comprises a dual-tube cylindrical capillary configuration; comprising a inner capillary 10, through which the supercritical fluid or gas flows from supply 30 into decompression chamber 40, and an outer capillary 12 confining between tubes 11 and 12 the interstitial flow of sheath liquid from supply 33. The sheath liquid functions to provide back pressure to the flow of supercritical fluid or gas at the exit of inner capillary 10 or to provide surface for condensation of expanding solutes originating from the supercritical fluid or gas stream. As in the dual-tube capillary configuration for sheath gas flows (FIG. 2) the lateral distance between the tips for capillary tubes 10 and 12 can be adjusted to produce different aerosol characteristics. This includes an alternative embodiment having capillary tube 10 withdrawn back to or beyond tee union 16. The flow tubes from supercritical fluid or gas supply 30 and sheath liquid supply 33 intersect at tee union 16 where the flow emerges therefrom in an orientation which is a function of the relative positioning of capillary tubes 10 and 12. This particular embodiment of the aerosol generator section of the present device utilizes resistive heating of the outer capillary 12, such outer capillary being, but not limited to, a conductive material such as nickel or stainless steel. Resistive heating of outer tube 12 is the source of heat for the liquid stream. Under some heating conditions the liquid is thermally nebulized to generate small liquid droplets or solute particles from dissolved components in the liquid stream. Capillary tubes 10 and 12 may have restrictor tips that are of capillary geometric, converging geometry, or supersonic nozzle geometry as shown respectively in FIGS. 3A, 3B and 3C, for capillary tube 10, respectively. Power supply 20 supplies sufficient electrical power to heat outer capillary 12, the highest resistance component in the electrical circuit, with electrical connections at points 21 and 22 and electrical isolation by ring insulator 13. Again, the aerosol generator is encased for safety by outer casing 28 and attached to the decompression chamber 40 at seal 29, such seal being a vacuum seal, e.g. an O-ring seal or other appropriate vacuum connection.

Figure 4A:
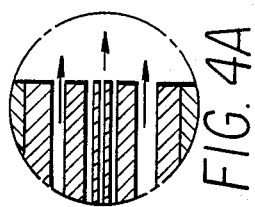
FIGS. 4A, 4B and 4C are enlarged views of alternative tip configurations for the FIG. 4 generator.
Figure 4B:
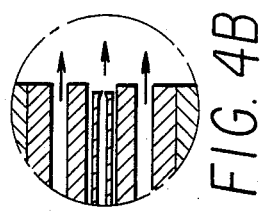
Figure 4C:
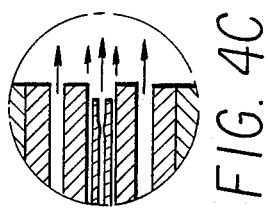
Figure 4:
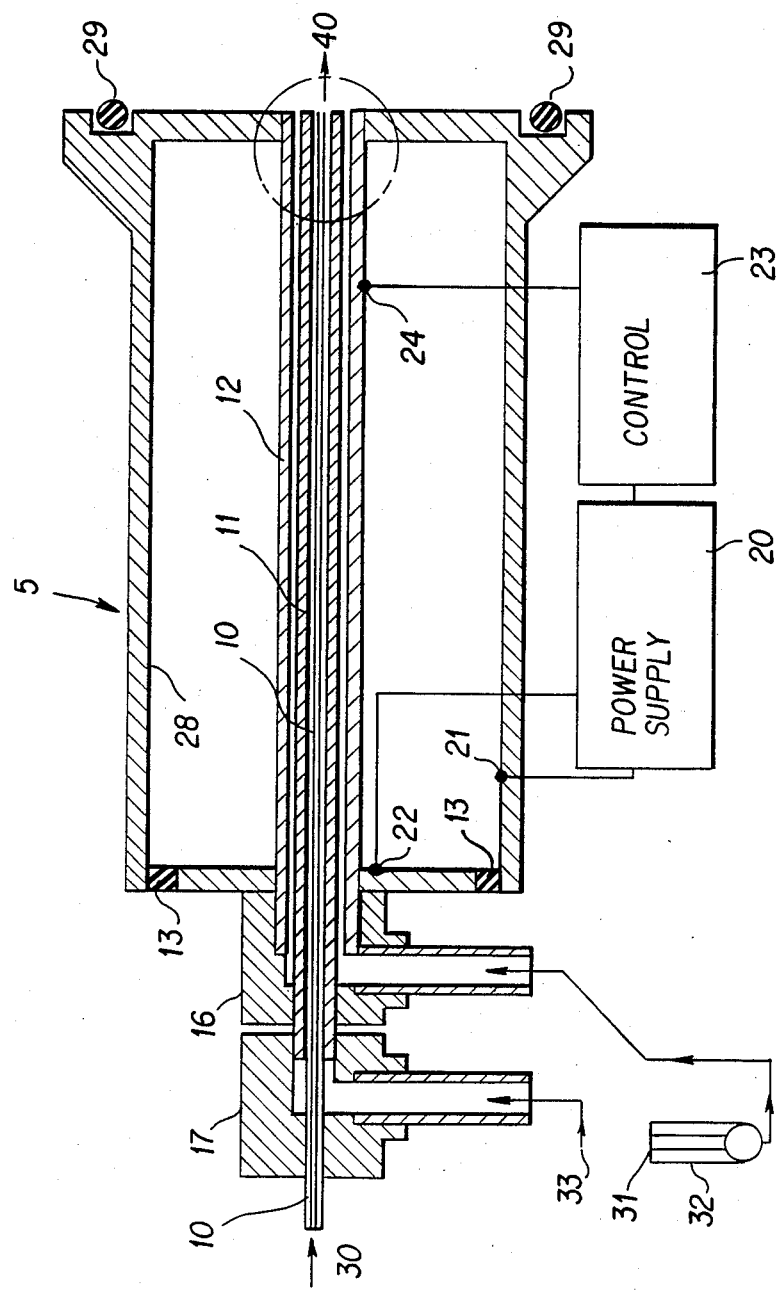
FIG. 4 is a view, similar to FIGS. 1-3, of a triple capillary decompression aerosol generator with concentric flow of both sheath gas and sheath liquid.

FIG. 4 illustrates a further typical embodiment of the invention wherein the aerosol generator 5 comprises a triple-tube cylindrical capillary configuration; comprising an inner capillary 10 through which supercritical fluid or gas flows into decompression chamber 40, an outer capillary 12 confining the interstitial flow of sheath gas from sheath gas supply 31, and an intermediate diameter capillary 11 confining the interstitial flow of sheath liquid from liquid supply 33. The sheath liquid functions to provide back pressure to the flow of supercritical fluid or gas at the exit of inner capillary 10 or provide surface for condensation of expanding solutes originating from the supercricital fluid or gas stream. The flow tubes from supercritical fluid or gas supply 30 and sheath liquid supply 33 intersect at a tee union 17 where the flow emerges therefrom in an orientation which is a function of the relative positioning of capillary tubes 10, 11 and 12. The sheath gas function is to conduct heat across the interstitial space between intermediate tube 11 and tube 12. Consequently it functions as a means of heating liquid flowing in the interstitial space between capillaries 10 and 11. The sheath gas is preferred to be, but not limited to, a high thermal conductive material such as helium or hydrogen. In addition, the sheath gas serves to sheath the aerosol as it expands into the decompression chamber 40. The flow of the sheath gas is controlled by sheath gas flow control 32. The concentric flow of supercritical fluid or gas from tee 17 intersects the flow of sheath gas from sheath gas supply 31 at tee union 16 where the flow emerges therefrom in an orientation which is a function of the relative position of capillary tubes 10, 11, and 12. This particular embodiment of the aerosol generator section of the present device utilizes resistive heating of the outer capillary 12, such outer capillary being, but not limited to, a conductive material such as nickel or stainless steel. Resistive heating of outer tube 12 is the source of heat to the liquid stream. Under some heating conditions the liquid is thermally nebulized to generate small liquid droplets or solute particles from dissolved components in the liquid stream. Any or all of the three capillary tubes 10, 11, and 12 may have restrictor tips that are of capillary geometry, converging geometry, or supersonic nozzle geometry as shown in FIGS. 4A, 4B and 4C, for capillary tube 10, respectively.

Power supply 20 supplies electrical power sufficient to heat the outer capillary tube 12, the highest resistance component in the electrical circuit, with electrical connections at points 21 and 22 and electrical isolation by ring insulator 13. Again, the aerosol generator is encased for safety by outer casing 28 and attached to the decompression chamber 40 at seal 29, such seal being a vacuum seal such as an 0-ring seal or other appropriate vacuum connection.

Figure 5:
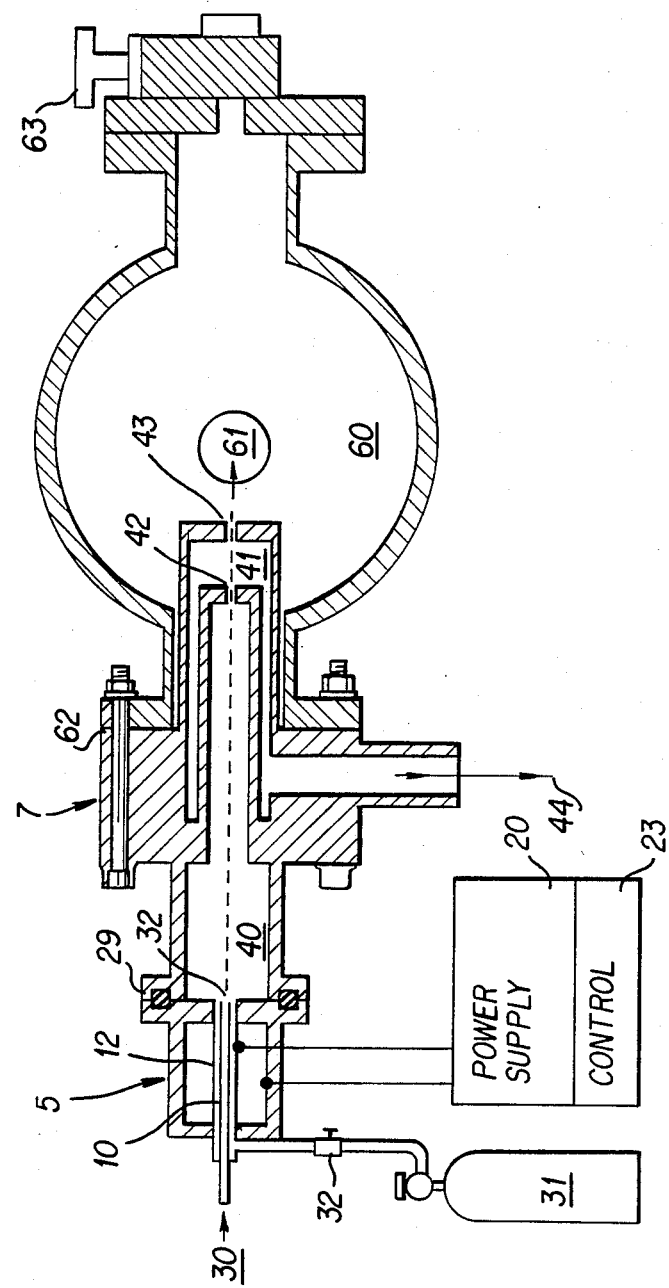
FIG. 5 is a diagrammatical sectional view of a SFC/MS device with aerosol generator, viscous flow expansion region, and a single stage particle beam separator.

FIG. 5 illustrates an embodiment of the present invention with single-stage particle beam enrichment. The device is composed of three components parts, namely, aerosol generator 5, a single-stage particle beam or momentum separator 7, and an ion source 60 for a typical mass spectrometer 61. Aerosol generator 5 is attached to decompression chamber 40 at sealed joint 29. The combination of aerosol generator and decompression chamber is attached to ion source chamber 60 via flange joint 62. Aerosol generator 5 illustrated in this figure is the dual capillary type as described with reference to FIG. 2. However, the interfacing of generator 5 with the compression chamber 40 is such that any aerosol generator as described with reference to FIGS. 1-4 or other aerosol generators whereby solute particles are generated at the end of a supercritical fluid or gas stream may be used. Aerosol generated by aerosol generator 5 expands axially in decompression chamber 40 and is carried in viscous flow downstream toward nozzle 42. The solute particles and vapor components of the aerosol are accelerated through nozzle 42, forming a high velocity aerosol beam along a longitudinal axis between nozzle 42 and skimmer 43. The aerosol beam is formed due to the pressure drop between decompression chamber 40 and vacuum chamber 41 which surround nozzle 42. Vacuum chamber 41 is evacuated by pump 44, generally a large pumping capacity mechanical vacuum pump such as a 400 L/min rotary pump. In the region between the axially aligned nozzle 42 and skimmer 43 the gas and vapor constituents of the aerosol expand significantly more rapidly than the solute particles. As a consequence of differential expansion of gases and particles, the particles are highly enriched at the axis of the expanding aerosol beam. The enriched solute particles are sampled into the ion source chamber 60 of the mass spectrometer through skimmer 43. An enriched solute particle beam is formed from the skimmer to the ionization region 61 of the mass spectrometer.

Figure 6:
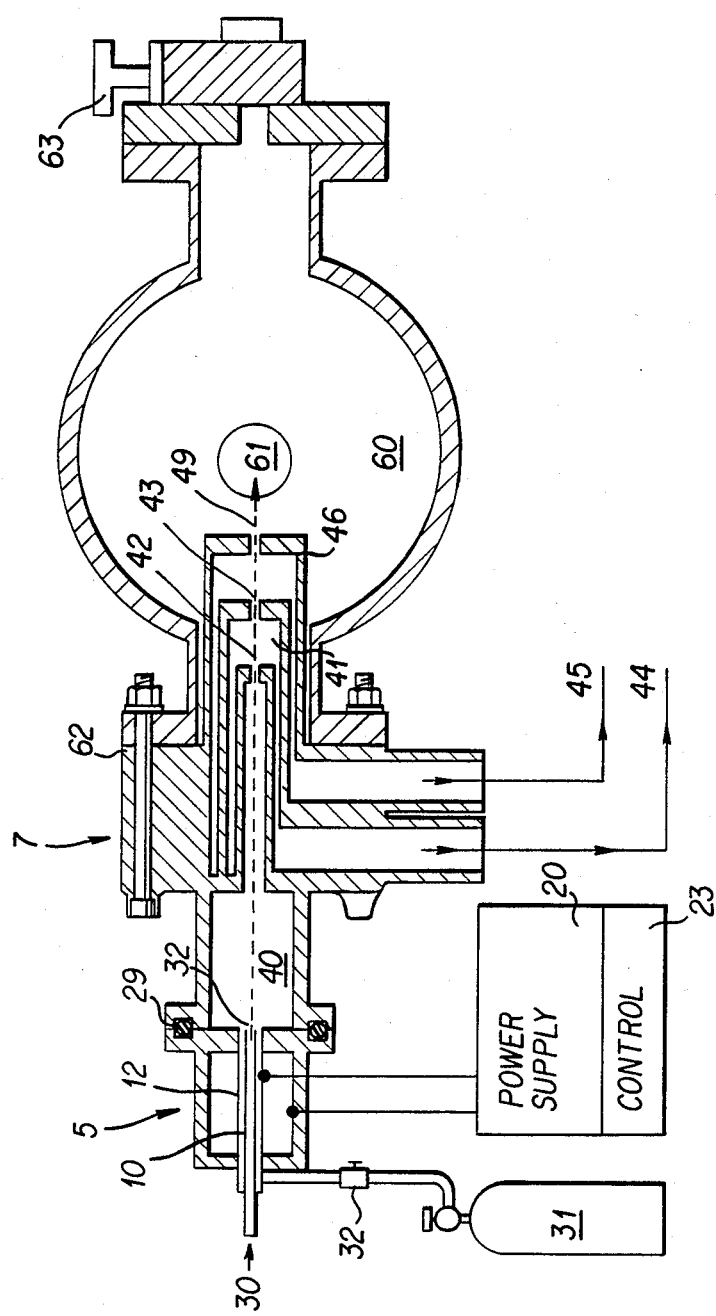
FIG. 6 is a view similar to FIG. 5 of a SFC/MS device with aerosol generator, viscous flow expansion region, and a dual stage particle beam separator.

FIG. 6 illustrates an embodiment of the present invention with dual-stage particle beam enrichment. As with FIG. 5, the device is composed of three component parts; namely, aerosol generator 5, dual-stage particle, beam or momentum separator 7, and the ion source chamber 60 of a typical mass spectrometer. The device is attached to ion source chamber 60 of the mass spectrometer via flange joint 62. Aerosol generator 5 is attached to the decompression chamber 40 at sealed joint 29. The aerosol generator 5, illustrated in this figure, is the dual capillary type as described with reference to FIG. 2, however, this interfacing device is adapted to operate with any aerosol generator 5 described with reference to FIGS. 1-4 or other aerosol generators whereby solute particles are generated at the end of the supercritical fluid or gas stream. The aerosol generated by aerosol generator 5 expands axially in decompression chamber 40 and is carried in viscous flow downstream toward nozzle 42. Solute particles and vapor components of the aerosol are accelerated through nozzle 42, forming a high velocity aerosol beam along a longitudinal axis between nozzle 42 and skimmer 43. The aerosol beam forms due to the pressure drop between decompression chamber 40 and vacuum chamber 41. The first vacuum chamber 41 is evacuated by vacuum pump 44, generally a large pumping capacity mechanical pump such as a 400 L/min rotary pump. In the region between axially aligned nozzle 42 and skimmer 43, the gas and vapor constituents of the aerosol expand more rapidly than the solute particles. As a consequence of differential expansion of gases and particles are highly enriched at the axis of the expanding aerosol beam. A second vacuum chamber 46, evacuated by pump 45, provides a higher degree of solute enrichment by pumping away additional aerosol vapor in the region between skimmer 43 and skimmer 49. The enriched solute particles are sampled into the ion source of the mass spectrometer through skimmer 49. An enriched solute particle beam is formed from the skimmer to the ionization region 61 of the mass spectrometer.

In operation, the device is connected to a supercritical fluid chromatograph or a liquid chromatograph and to a fluid source or sources as desired. Then, depending on the specific device involved, one, two or three fluid flows are used which are caused to flow through one, two or three tubes at the desired pressures, temperatures, and nozzle adjustments depending on the particular applications. The arrangements of the tube or tubes used and the characteristics of the fluids are selected and adjusted to produce specific aerosols having the desired properties. The aerosols slow to a ,viscous flow in the decompression chamber 40 and then are accelerated through the system by reason of the pressure drops, as previously described, into the ion source of the mass spectrometer (or into an alternate detector) where the aerosols are vaporized and ionized for subsequent mass analysis. They can be ionized by ion molecule reactions (CI) or by electron impaction ionization (EI) or by other modes of ionization known to those skilled in the art. Analysis of the ionized material is then carried out by the mass spectrometer by conventional mass spectrometry.

Although we have described the preferred embodiments of our invention, it is to be understood that it is capable of other adaptations and within the scope of the appended claims.

Having disclosed our invention, what we claim as new and to be secured by Letters Patent of the U.S. is:

1. A decompression aerosol generating device for obtaining solvent depleted solute particles of micron or submicron size in a well defined direction from sample dissolved in a supercritical fluid or carried in a gas stream, the sample containing volatile solvent or carrier and less volatile solute, said device comprising:
   a. a capillary tube to transport the supercritical fluid or gas into a decompression expansion chamber;
   b. fluid supply means for supplying supercritical fluid or gas at a pressure adequate to maintain the fluid in a supercritical state and to flow in such state to said capillary tube;
   c. thermal means for supplying or removing energy to heat or cool said capillary tube;
   d. control means for controlling the quantity of heat supplied or removed from said capillary tube;
   e. a decompression expansion chamber to receive fluid flow from said capillary tube which provides adequate space for high velocity gases and particles to reduce their velocity therein without substantial loss of the sample fluid due to particle impaction or settling;
   f. a nozzle restriction at the downstream side of said decompression expansion chamber, whereby flow of said aerosol therefrom is accelerated through said nozzle restriction, forming a high velocity solute particle beam; and
   g. a vacuum chamber downstream from the said nozzle restriction, whereby the aerosol flow emanating from the said nozzle restriction expands outwardly from the axis of said nozzle restriction, and vacuum pumping means maintaining a sufficiently low pressure in the said vacuum chamber to cause said outward expansion of said aerosol flow from said central axis;

whereby highly enriched solute particles are generated in said decompression expansion chamber and any carrier gases remaining in the vapor phase are separated from said highly enriched solute particles by accelerating the aerosol through said nozzle restriction.

2. An aerosol generating device as defined in claim 1, which further includes a further converging nozzle restriction means in said capillary tube for increasing the back pressure of the supercritical fluid or gas stream therein, said further converging nozzle restriction means restricting the fluid flow into said decompression expansion chamber.

3. A decompression aerosol generating device for obtaining solvent depleted solute particles of micron or submircon size in a well defined direction from sample dissolved in a supercritical fluid or carried in a gas stream, the sample containing volatile solvent or carrier and less volatile solute, said device comprising:
   a. an inner capillary tube to transport said supercritical fluid or gas into a decompression expansion chamber;
   b. an outer capillary tube to transport a heat conductive gas through an interstitial space between said inner and outer capillary tubes;
   c. first fluid supply means for supplying supercritical fluid at a pressure adequate to maintain said fluid in its supercritical phase as it flows to said inner capillary tube;
   d. second fluid supply means for supplying conductive sheath gas at a predetermined flow and pressure to said outer capillary tube;
   e. thermal means for supplying or removing energy to heat or cool said outer capillary tube;
   f. control means for controlling the amount of heat supplied or removed from said outer capillary tube;
   g. a decompression expansion chamber for receiving the flow from said inner capillary tube which provides adequate space for high velocity gases and particles to have their velocity reduced therein without significant loss of sample fluid due to particle impaction or settling;
   h. a nozzle restriction at the downstream side of said decompression expansion chamber, whereby the flow of said aerosol therefrom is accelerated through said nozzle restriction, forming a high velocity solute particle beam; and
   i. a vacuum chamber downstream, from said nozzle restriction whereby the aerosol flow emanating from said nozzle restriction expands outwardly from the axis of said nozzle restriction, and vacuum pumping means for maintaining a sufficiently low pressure in said vacuum chamber to cause said outward expansion of the aerosol flow in said vacuum chamber, wherein highly enriched solute particles are generated in said decompression expansion chamber and separated from the carrier gases remaining in the vapor phases by accelerating the aerosol through the said nozzle restriction.

4. A pneumatic aerosol generating device for obtaining solvent depleted solute particles of micron or submicron size in a well defined direction from sample dissolved in a supercritical fluid or carried in a gas stream, the sample containing volatile solvent or carrier and less volatile solute, said device comprising:
   a. an inner capillary tube to transport the supercritical fluid or gas into a decompression expansion chamber;
   b. an outer capillary tube to transport liquid through an interstitial space between said inner and outer capillary tubes;
   c. first fluid means for supplying supercritical fluid or gas to said inner capillary tube prior to merging streams;
   d. second fluid means for supplying liquid to said outer capillary tube prior to merging the two flow streams;
   e. thermal means for heating and cooling said outer capillary tube;
   f. control means for controlling the amount of heat energy supplied to or removed from said outer capillary tube;
   g. a decompression expansion chamber to receive fluid flow from said capillary tubes which provides adequate space for high velocity gases and particles to have their velocity reduced therein without significant loss of sample due to particle impaction or settling;

h. nozzle restriction means on the downstream side of said decompression expansion chamber for accelerating the flow of said aerosol from said decompression expansion chamber through said nozzle restriction means and forming a high velocity solute particle beam;

i. a vacuum chamber downstream from said nozzle restriction means, wherein aerosol flow emanating from said nozzle restriction means expands outwardly from a central said nozzle restriction means, a vacuum providing means producing said vacuum chamber and maintaining a sufficiently low pressure in said vacuum chamber for said aerosol expansion to occur so that highly enriched solute particles are generated in said decompression expansion chamber and separated from the carrier gases remaining in the vapor phase by accelerating the aerosol through said nozzle, restriction means.

5. A pneumatic and thermal aerosol generating device for obtaining solvent depleted solute particles of micron or submicron size in a well defined direction from sample dissolved in a supercritical fluid or carried in a gas stream, the sample containing volatile solvent or carrier and less volatile solute, said device comprising:

a. an inner capillary tube to transport the supercritical fluid or gas into a decompression expansion chamber;

b. an outer capillary tube concentrically surrounding said inner capillary tube;

c. an intermediate diameter capillary tube coaxial to said inner and outer capillary tube which is adapted to transport liquid through an interstitial space between said intermediate and said inner capillary tubes, said outer capillary tube adapted to transport conductive gas through an interstitial space between said outer and said intermediate capillary tubes;

d. a first fluid supply means for supplying supercritical fluid or gas to said inner capillary tube;

e. a second fluid supply means for supplying gas to the said outer capillary tube;

f. a third fluid supply means for supplying liquid to said intermediate capillary tube;

g. a thermal means for supplying or removing energy to heat or cool said outer capillary tube;

h. a control means for controlling the amount of heat supplied or removed from said outer capillary tube;

i. a decompression expansion chamber for receiving fluid flow from said capillary tubes and which provides adequate space for high velocity gases and particles to have their velocity reduced without substantial loss of fluid sample due to particle impaction or settling;

j. a nozzle restriction means at the downstream side of said decompression expansion chamber for accelerating the flow of said aerosol through said nozzle restriction means and forming a high velocity solute particle beam;

k. a vacuum chamber downstream from the said nozzle restriction means, whereby the aerosol flow emanating from the said nozzle restriction means expands outwardly from a central axis of said nozzle restriction means, vacuum producing means producing said vacuum and maintaining the pressure in the said vacuum chamber sufficiently low so that highly enriched solute particles received from in said decompression expansion chamber and are separated from the carrier gases remaining in the vapor phase by accelerating the aerosol through the said nozzle restriction means.

6. An aerosol generating device as defined in claims 1, 3, 4 or 5, which further includes a skimmer located in said vacuum chamber axially aligned with the nozzle restriction means whereby solute particles are preferentially sampled compared to carrier gas vapors by said skimmer.

7. aerosol generating device as defined in claim 6, which further includes an ion source region of a mass spectrometer.

8. An aerosol generating device as defined in claim 6, which further includes a second vacuum chamber downstream from said skimmer, said second vacuum chamber being evacuated by a second vacuum producing means to a lower absolute pressure in said second vacuum chamber than said first mentioned vacuum chamber.

9. An aerosol generating device as defined in claim 8, which further includes a second skimmer located in said second vacuum chamber axially aligned with said first mentioned skimmer, whereby the solute particles are preferentially sampled compared to the carrier gas vapors by said second skimmer.

10. An aerosol generating device as defined in claim 9 which further includes an ion source region of a mass spectrometer.

11. An aerosol generating device as defined in claim 6, comprising connection means adapted to be affixed directly to adapted to be affixed directly to a housing of a mass spectrometer.

12. An aerosol generating device as defined in claims 2, 3, or 4 which further includes a further converging restriction means in said inner capillary tube for increasing the back pressure of the supercritical fluid or gas stream therein, said further converging nozzle restriction means restricting the fluid flow into said decompression expansion chamber.

* * * * *